United States Patent [19]
Sabuda

[11] Patent Number: 6,048,301
[45] Date of Patent: Apr. 11, 2000

[54] METHOD AND DEVICE FOR STIMULATING BIOLOGICAL PROCESSES

[76] Inventor: Thomas J. Sabuda, 71 N. Edgewood Dr., Springville, N.Y. 14141

[21] Appl. No.: 09/114,861

[22] Filed: Jul. 13, 1998

[51] Int. Cl.[7] .......................... A61B 17/52; A61B 17/38; A61N 5/00; A61N 1/100
[52] U.S. Cl. ................... 600/9; 600/1; 600/15; 600/26; 606/33; 607/2; 607/100
[58] Field of Search ................. 600/1, 2, 15, 9, 600/26, 10, 11, 12, 13, 94; 607/100, 2, 1; 606/32, 33, 2, 3

[56] References Cited

U.S. PATENT DOCUMENTS

| 4,646,743 | 3/1987 | Parris | 128/396 |
|---|---|---|---|
| 4,838,850 | 6/1989 | Rosengart | 600/14 |
| 4,846,178 | 7/1989 | Fuxue et al. | 128/419 F |
| 4,930,504 | 6/1990 | Diamantopoulos et al. | 128/395 |
| 4,930,505 | 6/1990 | Hatje | 128/398 |
| 4,931,053 | 6/1990 | L'Esperance, Jr. | 606/2 |
| 4,998,532 | 3/1991 | Griffith | 128/419 F |
| 5,014,699 | 5/1991 | Pollack et al. | 128/419 F |
| 5,066,272 | 11/1991 | Eaton et al. | 600/9 |
| 5,084,909 | 1/1992 | Pollack | 378/64 |
| 5,086,770 | 2/1992 | Prangley | 128/395 |
| 5,092,835 | 3/1992 | Schurig et al. | 600/9 |
| 5,150,704 | 9/1992 | Tatebayashi et al. | 128/395 |
| 5,259,380 | 11/1993 | Mendes et al. | 607/115 |
| 5,269,746 | 12/1993 | Jacobson | 600/13 |
| 5,269,747 | 12/1993 | Erickson et al. | 600/14 |
| 5,480,374 | 1/1996 | Van Dick | 600/26 |
| 5,501,704 | 3/1996 | Chang et al. | 607/69 |
| 5,562,597 | 10/1996 | Van Dick | 600/26 |
| 5,584,863 | 12/1996 | Rauch et al. | 607/2 |
| 5,626,617 | 5/1997 | Brewitt | 607/2 |
| 5,792,184 | 8/1998 | Zhou et al. | 607/1 |

Primary Examiner—Cary O'Conner
Assistant Examiner—Navin Natnithithadha
Attorney, Agent, or Firm—Hodgson, Russ, Andrews, Woods & Goodyear, LLP

[57] ABSTRACT

A method and device for stimulating biological processes having a source of radiation disposed adjacent to a substantially ungrounded crystal. The device provides a structure for supporting a substantially ungrounded crystal adjacent to a source of radiation such that a crystal photon field is generated about the device. The invention also includes a method of stimulating biological processes by placing a subject within the crystal photon field created by the device.

17 Claims, 4 Drawing Sheets 6,048,301

METHOD AND DEVICE FOR STIMULATING BIOLOGICAL PROCESSES

FIELD OF INVENTION

This invention related to methods and devices for stimulating biological processes and specifically to a method and a device for emitting a crystal photon field about an ungrounded crystal and positioning a subject within the crystal photon field for stimulating biological processes.

BACKGROUND OF THE INVENTION

The use of electromagnetic fields (emfs) and, in particular, the use of weak emfs for stimulating biological processes is still in its infancy. That weak emfs affect biological processes is a concept that is gaining more acceptance by the scientific community which is beginning to realize that biological systems do not necessarily incorporate linear operating systems based on models developed by scientists.

Goodman and Henderson have demonstrated the changes in transcription and translation stages of protein synthesis following exposure to weak emfs (see Goodman, R.; Henderson, A. S., "Transcription and translation in cells exposed to extremely low frequency electromagnetic fields," *Bioelectrochemistry and Bioenergetics*, 1991; 25: 335–355). Adey has proposed that weak emfs, initially considered too weak to interact with biomolecular systems, can interact at the cell surface. Adey indicated that there is increasing evidence that these events at the cell surface "relate to quantum states and resonant responses in biomolecular systems, and not to equilibrium thermodynamics associated with thermal energy exchanges and tissue heating" (see Adey, W. R., "Biological Effects of Electromagnetic Fields," *Journal of Cellular Biochemistry*, 1993; 51: 410–416). Bassett pointed out that the dominant biochemical models do not have all the answers and have overlooked the electrical aspects of the cells. He also stated that the field of bioelectromagnetics is only in its infancy and there are still unknown subtleties of the manner in which biological systems interact with emfs. The tendency of physicists and engineers to oversimplify exceedingly complex biosystems to fit the standard equations of their disciplines is not advisable in the context of the many interactive factors that Bassett enumerates and that determine the manner in which biological systems respond to biolelectromagnetic stimuli (see Bassett, C. Andrews, "Beneficial Effects of Electromagnetic Fields," *Journal of Cellular Biochemistry*, 1993; 51: 387–393). Frey discusses how a living organism can be expected to respond to emfs by comparing it to a radio receiver that ignores all non-resonant frequencies even if they are strong. However, a weak resonant frequency will interfere with the radio reception of a strong electromagnetic signal. Similarly, if we expose a living organism to a very weak electromagnetic signal, if the signal is appropriately "tuned," it could facilitate or interfere with normal function (see Frey, Allan H., "Electromagnetic field interactions with biological systems," *FASEB Journal*, 1993; 7: 272–281).

Many prior art devices and methods for stimulating biological processes employing emfs have been developed. U.S. Pat. No. 5,562,597 to VanDick (1996) discloses a method and apparatus of generating a weak emf about an electrical conductor and a quartz crystal employing electrical impulses generated by a pulse generator synthesizing complicated waveforms. In U.S. Pat. No. 5,269,746 to Jacobson (1993), a treatment method is disclosed utilizing a weak, low frequency, alternating magnetic field generated about an electrically conductive wire. U.S. Pat. No. 5,092,835 to Schurig et al. (1992) discloses a method and an apparatus to apply a constant magnetic field to the brain in conjunction with electric signals delivered to the body via skin contacting electrodes. Devices and methods (which require focusing radiation on tissues) for biostimulation of tissues employing lasers and/or light emitting diodes (leds) for irradiating relatively small tissue areas are disclosed in U.S. Pat. Nos. 4,930,504 to Diamantopoulos et al. (1990), and in 5,259,380 to Mendes et al. (1993), and in 4,931,053 to L'Esperance, Jr. (1990). An electrotherapeutic system employing pulsed radio frequency signals delivered via tissue contacting applicators is disclosed in U.S. Pat. No. 5,584,863 to Rauch et al. (1996). U.S. Pat. No. 4,838,850 to Rosengart (1989) discloses an electromedical treatment apparatus which employs a magnetic field generator and an electric field generator in the apparatus. U.S. Pat. No. 5,014,699 to Pollack et al. (1991) discloses an electromagnetic method and apparatus for healing living tissues which employs pulsed electrical signals coacting with a coil worn or carried by a patient. U.S. Pat. No. 4,846,178 to Fuxue et al. (1989) discloses an electric field therapeutic apparatus requiring electrode contact with an injured body part. U.S. Pat. No. 5,501,704 to Chang et al. (1996) discloses a method for applying low energy emissions employing an emitter to generate the emissions which are applied to a patient by means of a probe. U.S. Pat. No. 5,066,272 to Eaton et al. (1991) discloses a magnetic nerve stimulator which employs a high voltage discharge through a coil placed near a patient's head.

Since antiquity healing powers have been attributed to pure crystals of various minerals. Today, many healers use crystals to treat ailments with varying degrees of success. Methods of using healing crystals comprise wearing the crystal as one would wear an item of jewelry, sleeping with the crystal, or placing crystals on selected body locations of someone in the supine position. Attempts to study the healing properties of crystals have, for the most part, led to the conclusion that any effect of crystals on a person's ailments is due to a placebo effect. These studies did not make any provision for providing an incident radiation of sufficient intensity and providing the incident radiation for a time period of sufficient duration to affect biological processes.

In his book, *Paramagnetism*, Callahan discusses biostimulation within another context. His observations lead him to the conclusion that rocks and minerals exert a stimulating effect on plant life. He also develops the thesis that ancient civilizations recognized that rocks and minerals interact with radiations emanating from the heavens and utilized that concept in their agricultural practices (see Callahan, Philip S., *Paramagnetism;* Metairie, La.: Acres U.S.A., 1995).

The crystals present in rocks and minerals can perform any combination of the following actions on an electromagnetic radiation incident to the surface of the rock or mineral: transmit, reflect, retroflect, refract, polarize, and modulate. Some crystalline structures have inherent optical activity due to their ability to act as polarization rotators. Also, many organic materials exhibit optical activity. Materials with inherently helical molecules in their composition display an optical activity in response to an incident electromagnetic radiation. Examples of such materials are quartz, tellurium, tellurium oxide, and selenium. These optical rotators circularly polarize electromagnetic waves incident to them. Additionally, the minerals quartz and calcite are composed of uniaxial birefringent crystals which are double refracting so that two separate beams are created from an incident beam. Each beam so created is totally polarized and orthogonal with respect to the other beam. Some crystals in minerals also modulate an incident electromagnetic radiation.

A crystal plurally modifies incident electromagnetic radiation(s) as the radiation passes through the crystal. Consequently, the incident radiation's impetus generates a radiation complex about the ungrounded crystal. The applicant of the present invention gives the aforementioned "radiation complex about the ungrounded crystal" the designation "crystal photon field" which is composed of photons and the photons' associated quanta and electromagnetic waves. The crystal photon field (cpf), having qualitative differences, is distinguished from an emf generated about an electrical current carrying conductor and the radiations generated from lasers and light emitting diodes (leds).

Accordingly, it is desirable to produce a safe and effective device for stimulating biological processes employing a biologically stimulating vector having no component of an emf generated about conductors carrying electrical current emitted from engineered pulse generators. It is additionally desirable to produce a safe and effective device for stimulating biological processes employing a biologically stimulating vector not having treatment area size limitations inherent with laser radiation devices and led radiation devices which additionally require focusing the emitted radiation beam to the treatment area. It is evident from the foregoing that there is a need for an effective device and an effective method for stimulating biological processes not employing engineered, pulse generator emitted emfs about electrical conductors and the small treatment area of the emitted radiation beams and the emitted radiation beam focusing requirements of laser radiation devices and light emitting diode radiation devices.

SUMMARY OF THE INVENTION

In accordance with the present invention, a device for stimulating biological processes employing a distinctive crystal photon field having considerable advantage over prior art is provided. In an exemplary embodiment of the invention, the deficiencies of prior art systems are overcome in a system generating a distinctive, non-engineered biostimulating vector (the crystal photon field) that requires no focusing, covers an extremely large treatment area, is devoid of an emf generated about an electrical current carrying conductor, and is utilized without tissue contact. The exemplary embodiment includes a connector to an electrical power source; a low pressure mercury vapor lamp generating a radiation consisting of the radiation wavelengths 253.7 nm, 320 nm, 365 nm, 404.7 nm, 435.8 nm, and 546.1 nm and a rose quartz crystal. As the radiation is incident to the rose quartz crystal's surface, the crystal emits a cpf about itself. The applicant of the present invention discovered that this so generated cpf stimulates biological processes placed within the cpf.

OBJECTS AND ADVANTAGES

Accordingly, several objects and advantages of the present invention and method are:

(a) to provide a device and method for emitting a cpf about an ungrounded crystal for stimulating biological processes;

(b) to provide a device for emitting a cpf about an ungrounded crystal for stimulating biological processes that is portable and light in weight;

(c) to provide a device for emitting a cpf about an ungrounded crystal for stimulating biological processes that is simple and safe to operate;

(d) to provide a device for emitting a cpf about an ungrounded crystal for stimulating biological processes that employs no tissue contact;

(e) to provide a device for emitting a cpf about an ungrounded crystal for stimulating biological processes without employing pulse generator emitted emfs;

(f) to provide a device for emitting a cpf about an ungrounded crystal for stimulating biological processes without employing laser emitted radiations and/or led emitted radiations;

(g) to provide a method for stimulating biological processes that does not require restricting the subject.

The above and yet other objects and advantages of the present invention and method will become apparent from the hereinafter set forth Brief Description of the Drawings, Utilization Procedure, Theory of System Operation, and Claims.

BRIEF DESCRIPTION OF THE DRAWINGS

With reference to FIG. 1, there is shown an electrical power source 10 having connection to a radiation source 11. A radiation 12 radiated by the radiation source 11 is located between the radiation source 11 and a crystal 13 and the radiation 12 is contiguous upon the crystal 13. A crystal photon field 14 (cpf) emitted from the crystal 13 is disposed about the crystal 13 and a subject 15 is positioned within the cpf 14 for stimulating biological processes of the subject 15.

Figure 1:
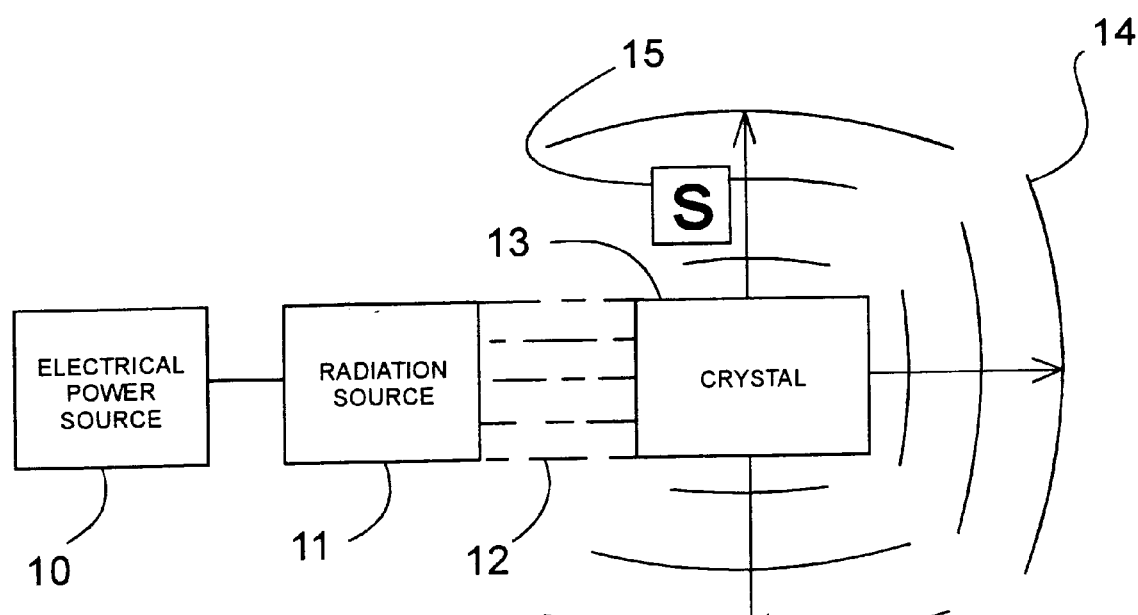
FIG. 1 shows a schematic diagram of the present invention.

The radiation source 11 is preferably a low pressure mercury vapor lamp (lpmv lamp). The lpmv lamp produces radiation 12 in the ultraviolet portion of the spectrum. The radiation 12 from the lpmv lamp comprises the following radiation wavelengths and corresponding radiation wavelength composition percentages: 253.7 nanometers (nm) (86%), 320 nm (2%), 365 nm (2%), 404.7 nm (2%), 435.8 nm (5%), and 546.1 nm (3%). The UV radiation 12 is incident upon the crystal 13 which is preferably a rose quartz type crystal. The aspect of the UV radiation 12 being upon the crystal 13 has an intensity consisting of 50 microwatts per square centimeter for radiation wavelengths less than 300 nm and 100 microwatts per square centimeter for the radiation wavelengths greater than 300 nm A cpf 14 is disposed about the crystal 13 and the subject 15 is positioned within the cpf 14 for stimulating biological processes of the subject 15.

Figure 2A:
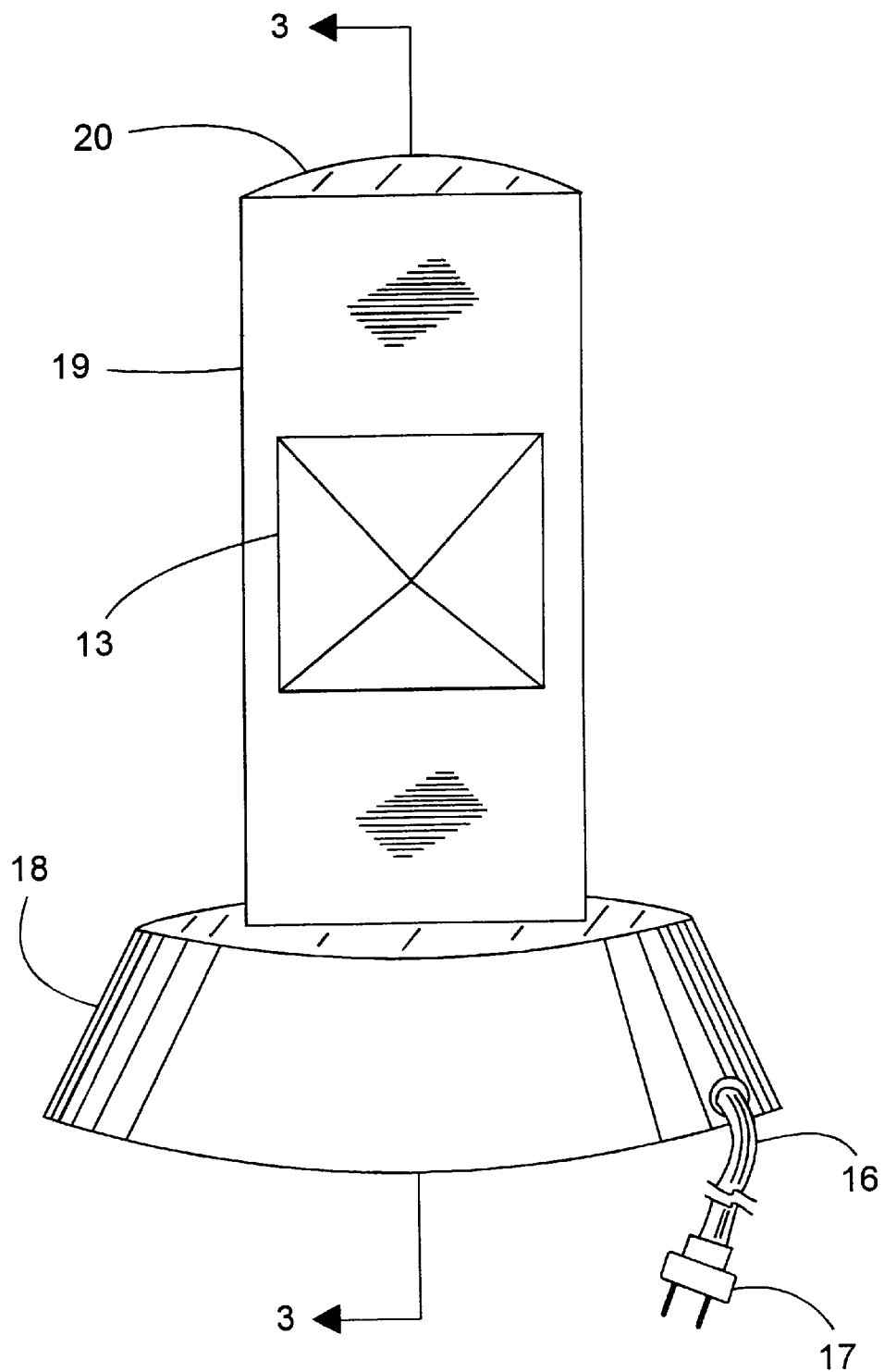
FIG. 2A shows a front elevational view of the preferred embodiment of the present invention.
Figure 2B:
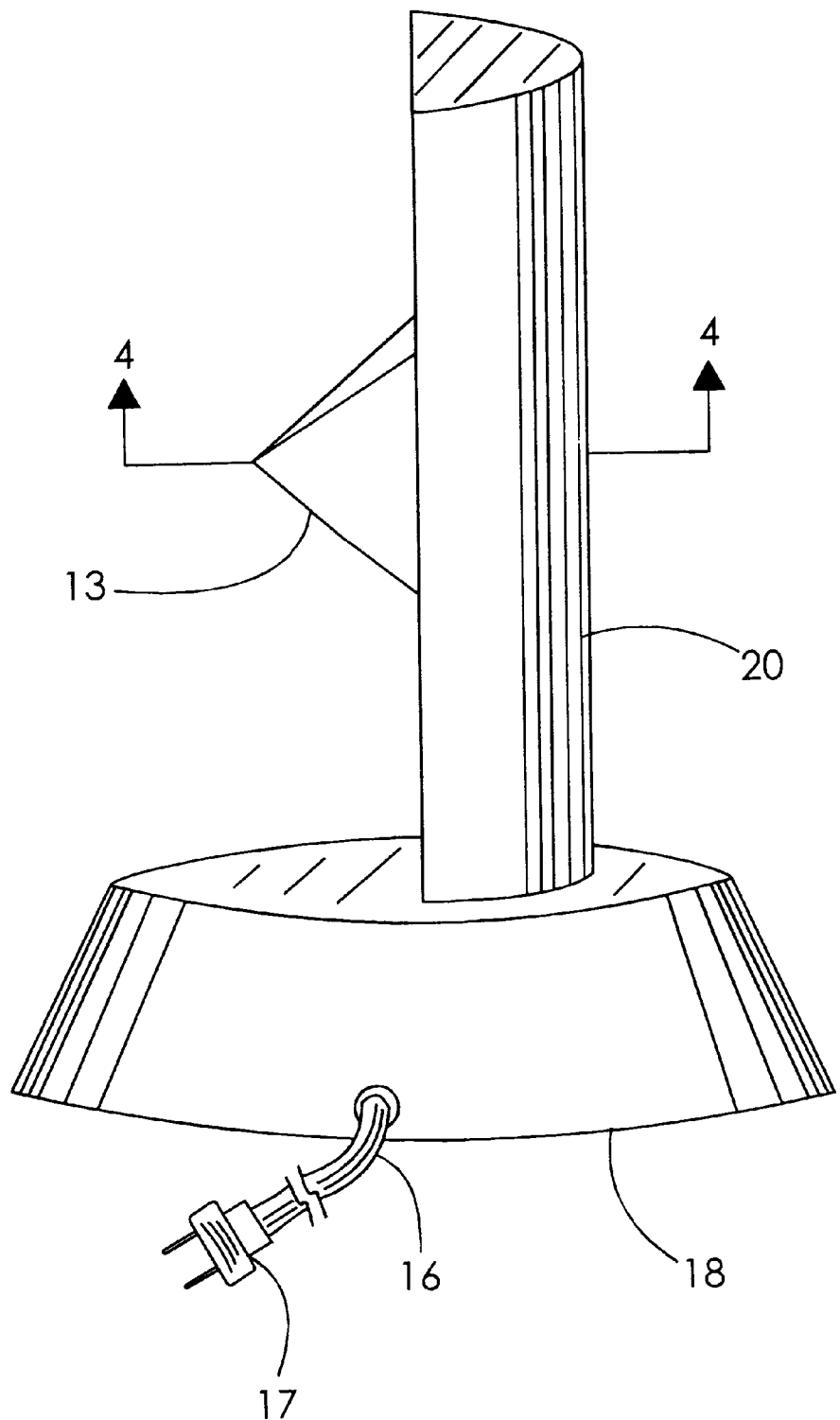
FIG. 2B shows a side elevations view of FIG. 2A.

FIG. 2A and FIG. 2B show the preferred embodiment according to the present invention. An electrical conducting cord 16 has a terminal connection at a first end to an electrical plug 17 and, at a second end, the electrical conducting cord 16 has connection within a pedestal 18. The pedestal 18 provides support for and is joined to a front member 19 which is substantially electrically non-conductive and to a rear member 20. The front member 19 comprises a positioning means for positioning the crystal 13 which is preferably pyramidally shaped. The rear member 20 has means for joining to the front member 19.

Figure 3:
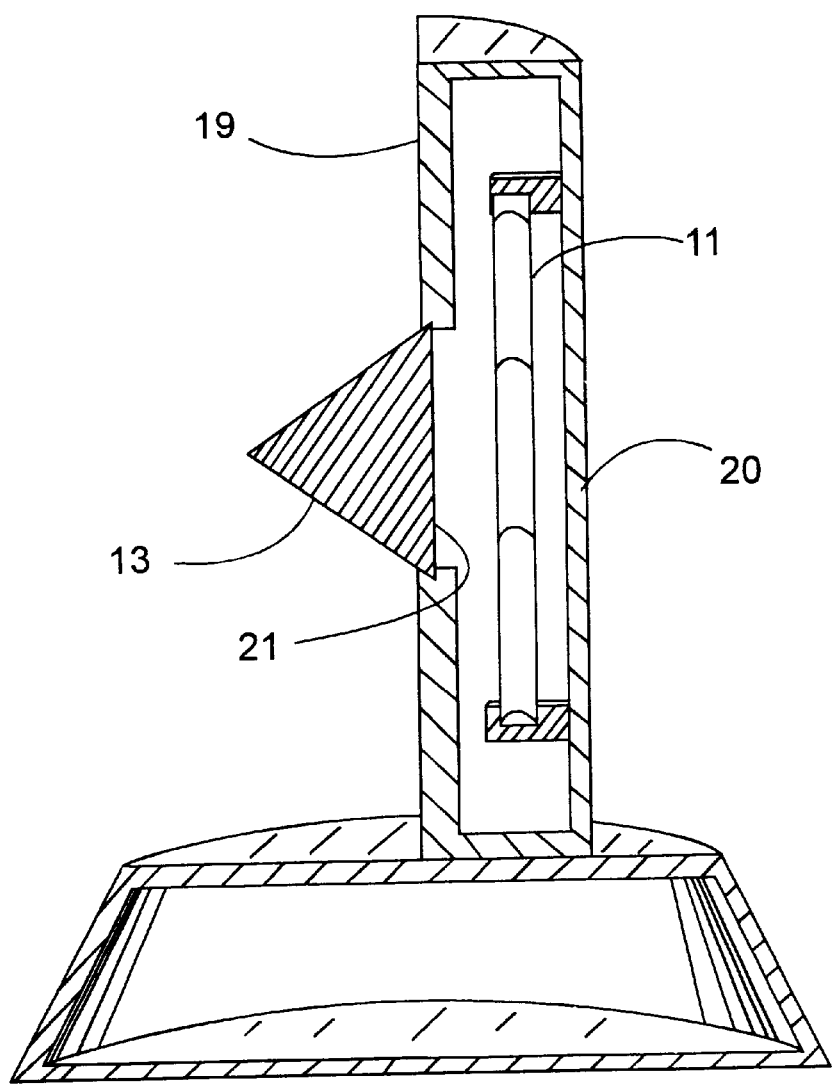
FIG. 3 shows a sectional view of the preferred embodiment of FIG. 2A taken through line 3—3.
Figure 4:
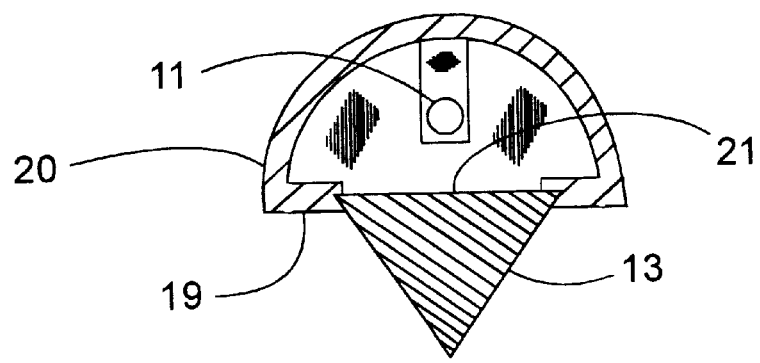
FIG. 4 shows a cross sectional view of the preferred embodiment of FIG. 2B taken through the line 4—4.

FIG. 3 and FIG. 4 show the position of a base face 21 of the crystal 13 and the position of the radiation source 11.

FIG. 3 shows the radiation source 11 comprising a tubular structure, and long axis of which lies parallel to the plane of the base face 21. FIG. 4 shows the radiation source 11 in proximity to the center of the base face 21. The crystal 13, being substantially ungrounded, is engaged within the edges of the front member 19 surrounding the crystal 13. Additionally, FIG. 3 shows the rear member 20 having connection to the radiation source 11 and comprising a positioning means for positioning the radiation source 11 in proximity to the base face 21.

FIG. 4 shows the lpmv lamp 11 having a position in proximity to the approximate center of the base face 21.

UTILIZATION PROCEDURE

In the operational mode of the preferred embodiment of the present invention, the electrical plug 17 has connection to the electrical power source 10. In the continuous mode of operation of the preferred embodiment of the present invention, the electrical power is moving through the electrical plug 17, through the electrical conducting cord 16, and into the radiation source 11 and causing the radiation source 11 to be in an energized state. While in the energized state, the radiation source 11 generates the UV radiation 12 and the UV radiation 12 is allowed to be upon the base face 21. While the UV radiation 12 is upon the base face 21, the crystal 13 emits the cpf 13 about itself. A subject 15, such as a human mammal, a non-human mammal, a plant, and an in vitro biological entity, is positioned within the cpf 14. A position of the subject 15 need not be fixed and a distance between the crystal 13 and the position of the subject 15 has variance and usually consists of less than 40 feet in a routine operational situation. A time duration also has variance and usually consists of less than sixty minutes. The objective status of the subject 15 and the subjective status of the subject 15 determine the time duration for stimulating biological processed.

THEORY OF SYSTEM OPERATION

A general theory for the basis of the cpf 14 and the cpf's influence on biological processes as proposed herein. The cpf 14, generated by the impetus of the radiation 12 upon the crystal 13, is comprised of photons and the photons' associated electromagnetic waves emitted from the crystal 13 as the result of at least three phenomena: 1) photons emitted as the result of electrons being excited by the radiation 12 and returning to a ground state; 2) photons with at least one polarization state emitted as the result of the photons gaining the polarization state during a passage through the crystal 13; 3) photons emitted as the result of the splitting of a parent photon during a passage of the parent photon through the crystal 13. The three phenomena so cited give differentiating qualitative aspects to the cpf 14 and these qualitative aspects comprise the aspects that differentiate the cpf 14 from the emfs characteristic of pulse generators, lasers, and light emitting diodes.

Additionally, the three phenomena result in the emission of specific quanta. Since most forms of photoexcitation are quantum specific, each quantum emitted from the crystal 13 has the potential to be selectively absorbed and to interact with the many components involved in biological processes. Each frequency emitted from the crystal 13 has the potential to resonate with one of the many frequency components involved in biological processes. Utilization of the cpf 14 of the system and of the preferred embodiment of the present invention to stimulate biological processes in painful tissues and in inflamed tissues results in some or all of the following objectively observed and subjectively observed tissue changes: decreased swelling, decreased pain, increased palpable warmth, increased sensations of warmth, and increased sense of well-being. The observed tissue changes may result from increased circulation to and increased circulation within the tissues studied. Additionally, the observed tissue changes suggest an increased level of aerobic cellular respiration.

While the description of the preferred embodiment of the present invention contains many specificities, these should not be construed as limitations on the scope of the invention, but rather as an exemplification of the preferred embodiment thereof. Many other variations are possible and that are within the scope and spirit of the invention. Other radiation sources may be selected from the group consisting of, but not limited to, x-ray generators, long wavelength ultraviolet generators, and infrared generators. Multiple radiation sources may be utilized simultaneously. Other crystals may be selected from the group consisting of, but not limited to, other silicates, phosphates, carbonates, diamonds, synthetic crystals, oxides, organic crystals, crystals in solution, and crystal aggregates such as granite. Multiple crystals may be utilized simultaneously. Also, the crystal may assume a shape selected from, but not limited to, cube, obelisk, hexahedron, disk and uncut crystalline form. A battery may comprise the power source. The subject may be selected from a group consisting of human mammal, non-human mammal, plant, and in vitro biological entity. From the foregoing, it will be obvious to those skilled in the art that various modifications in the above-described apparatus can be made without departing from the spirit or essential characteristics thereof. Present embodiments, therefore are to be considered in all respects as illustrative and not restrictive, the scope of the invention being indicated by the appended claims rather than by the foregoing description, and all changes which come within the meaning and range of equivalence of the claims are therefore intended to be embraced therein.

What is claimed:

1. An apparatus for stimulating biological processes, comprising:
   at least one angled crystal;
   a source of radiation disposed adjacent to the angled crystal, the source of radiation emitting radiation incident upon the crystal and having a wavelength between $10^{-3}$ nm and 770 nm; and,
   wherein a substantially heat free crystal photon field is generated about the angled crystal.

2. The apparatus of claim 1, wherein the radiation source is a low pressure mercury vapor lamp.

3. The apparatus of claim 1, wherein the crystal is formed out of organic molecules.

4. The apparatus of claim 1, wherein the crystal comprises at least one element selected from the group consisting of aluminum, antimony, barium, beryllium, carbon, chlorine, chromium, cobalt, copper, fluorine, gold, hydrogen, iron, lead, mercury, magnesium, manganese, nickel, nitrogen, oxygen, phosphorous, potassium, selenium, silicon, silver, sodium, sulfur, tellurium, titanium, vanadium, and zinc.

5. The apparatus of claim 1, wherein the crystal comprises at least one ion selected from the group consisting of arsenate, borate, calcium, carbonate, chloride, chromate, ferrous, ferric, fluoride, molybdate, nitrate, nitrite, oxide, phosphate, potassium, silicate, silver, sodium, sulfide, sulfate, sulfite, tungstenate, vanadate, and zinc.

6. The apparatus of claim 1, wherein the crystal is comprised of a mineral selected from the group consisting of albite, amethyst, apatite, aragonite, barite, beryl, biotite, calcite, chalcopyrite, corundum, diamond, fluroite, garnet, halite, ice, malichite, opal, pyrite, quartz, tellurium oxide, and titanite.

7. The apparatus of claim 1, wherein the crystal is synthetic.

8. The apparatus of claim 1, wherein the crystal is ungrounded.

9. A method of stimulating biological processes in a subject, comprising:
   a) applying radiation to at least one angled crystal, the radiation having a wavelength between $10^{-3}$ nm and 770 nm, whereby the crystal is emitting a crystal photon field about itself, and,
   b) positioning the subject within the crystal photon field.

10. The method of claim 9, wherein the radiation is generated by a low pressure mercury vapor lamp.

11. The method of claim 9, wherein the crystal is formed out of organic molecules.

12. The method of claim 9, wherein the crystal comprises at least one element selected from the group consisting of aluminum, antimony, barium, beryllium, carbon, chlorine, chromium, cobalt, copper, fluorine, gold, hydrogen, iron, lead, mercury, magnesium, manganese, nickel, nitrogen, oxygen, phosphorous, potassium, selenium, silicon, silver, sodium, sulfur, tellurium, titanium, vanadium, and zinc.

13. The method of claim 9, wherein the crystal comprises at least one ion selected from the group consisting of arsenate, borate, calcium, carbonate, chloride, chromate, ferrous, ferric, fluoride, molybdate, nitrate, nitrite, oxide, phosphate, potassium, silicate, silver, sodium, sulfide, sulfate, sulfite, tungstenate, vanadate, and zinc.

14. The method of claim 9, wherein the crystal is comprised of a mineral selected from the group consisting of albite, amethyst, apatite, aragonite, barite, beryl, biotite, calcite, chalcopyrite, corundum, diamond, fluroite, garnet, halite, ice, malichite, opal, pyrite, quartz, tellurium oxide, and titanite.

15. The method of claim 9, wherein the crystal is synthetic.

16. The method of claim 9, wherein the crystal is ungrounded.

17. The method of claim 9, wherein the subject comprises a living organism.

\* \* \* \* \*